Figure 1:
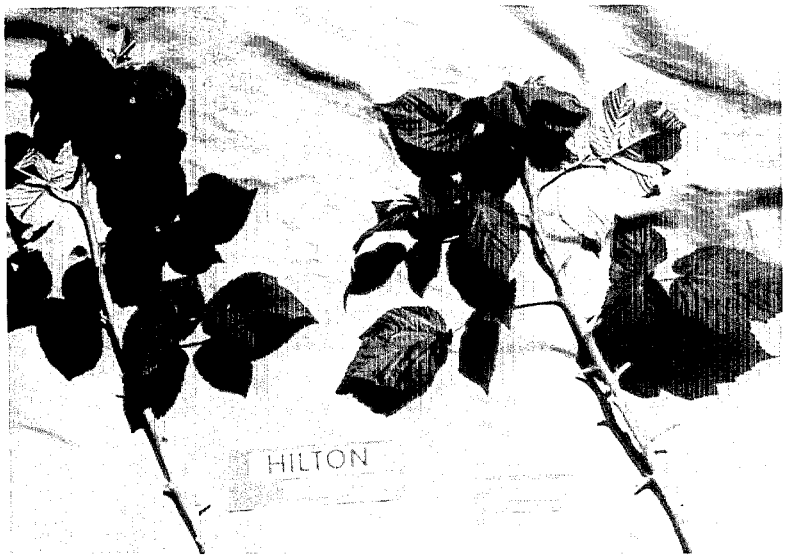

United States Patent [19]

Sanford et al.

[11] Patent Number: Plant 5,404

[45] Date of Patent: Feb. 12, 1985

[54] RED RASPBERRY, N.Y. 883

[75] Inventors: John C. Sanford, Geneva; Donald K. Ourecky, Rochester, both of N.Y.

[73] Assignee: Cornell Research Foundation, Inc., Ithaca, N.Y.

[21] Appl. No.: 418,964

[22] Filed: Sep. 16, 1982

[51] Int. Cl.[3] ..... A01H 5/03

[52] U.S. Cl. ..... Plt./46

[58] Field of Search ..... Plt./46

*Primary Examiner*—Robert E. Bagwill

[57] ABSTRACT

A red raspberry plant which has a high yield of large, well displayed fruit.

5 Drawing Figures

SUMMARY

This invention is a new and distinct variety of summer-bearing red raspberry which is exceptional for its large fruit, its high yield potential, and its well-displayed and easy to harvest crop.

ORIGIN

This new cultivar was developed by the Small Fruits Breeding program of the Department of Pomology and Viticulture, Cornell University, New York State Agricultural Experiment Station, Geneva, NY. The cross was Hilton×N.Y. 598 ('Newburgh'×'September'), and was made in 1963. The specific clone was selected in 1966, and has been extensively tested under the number N.Y. 883.

DESCRIPTION

N.Y. 883 has stout green glabrous primocanes, with very sparse, small spines. Spines are concentrated at the base of the canes, and are absent on the upper portions of the cane. Spines are green with slightly darkened tips. Fully expanded leaves are large, broad, flat, and dark green. They are born horizontally from the cane. Dormant axillary buds are characteristically large.

The stem color of an actively-growing primocane corresponds approximately to green 143C on the color chart of The Royal Horticultural Society, London, England (all color numbers herein refer to said chart). During the dormant season, the terminal quarter of the primocane turns purple (red-purple 59A). Below that point, the stem color becomes brown (greyed-orange 165A). There is little or no waxy bloom on the upper three quarters of the primocane. Primocanes of N.Y. 883 typically attain lengths of 110 cm to 180 cm (average about 150 cm) and basal diameters of 10 mm to 17 mm (average about 13 mm) on soils of medium fertility.

Root suckering is light and plant vigor is average. Fruit are highly visible and are not hidden from view by foliage, due to delayed primocane growth prior to fruiting and due to reduced foliage on the fruiting laterals.

Fruit are very large, and tend to be equal to or larger than 'Hilton' in size and weight. Berries of N.Y. 883 typically range from 15 mm×30 mm (5-6 grams in weight) down to 10 mm×15 mm (3-4 grams in weight). The median fruit size is approximately 12×30 mm (4-16 grams). Fruit are bright red (42A), with a long conic shape, approximately twice as long as wide. Fruit yields can be very exceptional. When bearing a heavy crop, canes require support. The fruit torus is long, pointed, and pink on a long pedicel. The fruit is juicy and has a large cavity, but retains good firmness and conerence. At Geneva, N.Y., fruit ripen in mid-season, i.e. early in July.

N.Y. 883 is morphologically very similar to its maternal parent, 'Hilton'. It can be distinguished from 'Hilton' by its green rather than purple spines, its larger axillary buds, and its year-old wood which is darker brown and less silvery, and which shows more peeling of the epidermis. It is also distinguishable because 'Hilton' has softer fruit, darker and duller-colored fruit, and more uniformly sized drupelets. N.Y. 883 has a milder flavor than 'Hilton' and has fruit which clasp the torus more firmly than 'Hilton'.

Plants have very low susceptibility to the aphid *Amphorophora agathonica* Hottes, and the aphid has great difficulty colonizing greenhouse plants.

N.Y. 883 is easily propagated in vitro, using standard red raspberry tissue culture media.

DESCRIPTION OF PHOTOGRAPHS

The following describes the accompanying photographs, documenting the unique morphological features characterizing this new culture.

FIG. 1—A primocane of N.Y. 883 is shown on the right, next to a primocane of Hilton on the left. N.Y. 883 has primocanes which are essentially identical to Hilton, with broad, dark green, horizontal leaves and stems which are glabrous except at the base. However, the basal spines of N.Y. 883 are green, while the spines of Hilton are purple.

Figure 2:
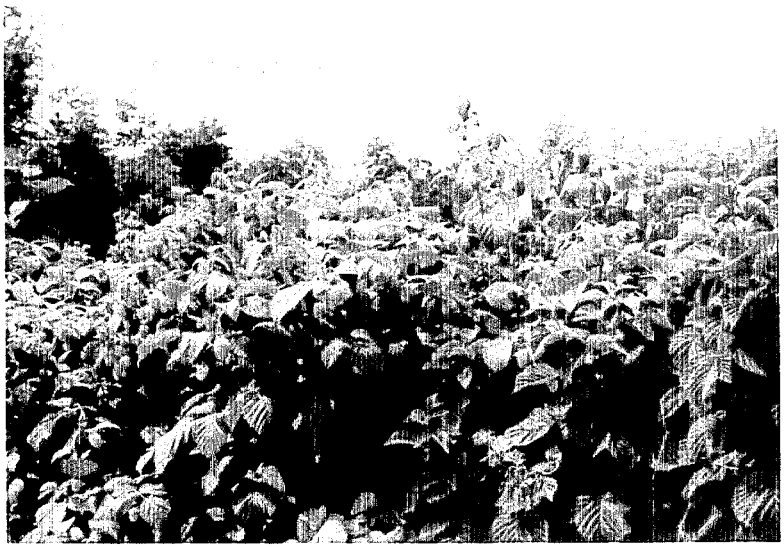

FIG. 2—A field planting of N.Y. 883 is shown. Delayed primocane growth and reducing fruiting cane foliage results in highly exposed, easy to find fruit. Note that the fruit hang pendantly on the fruiting canes.

Figure 3:
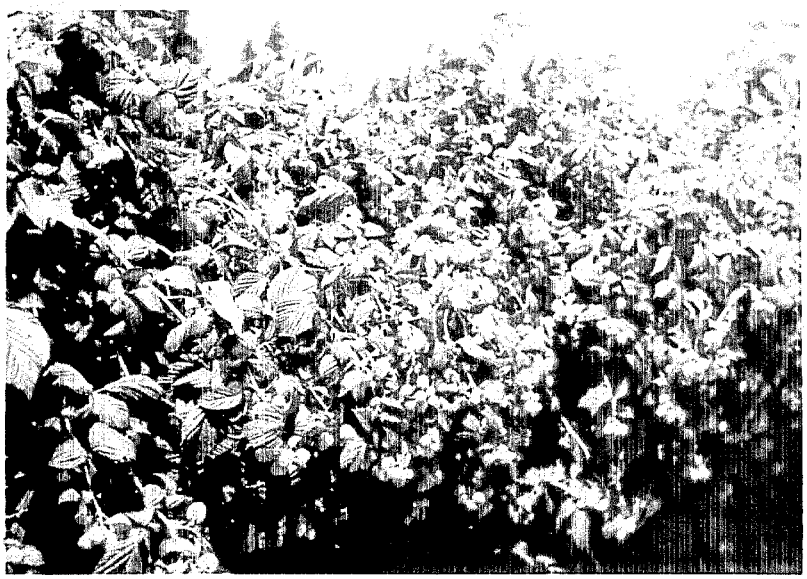

FIG. 3—A field planting of N.Y. 883 at Vancouver, Wash. Under these conditions, extremely large fruit and extremely heavy yields can be observed. Note that canes are bending down from a support wire, and that such support is required with a very heavy crop. Yield data indicated that N.Y. 883 can yield over 7 tons per acre. Berry size and yields were dramatically superior to the 13 other varieties and selections tested, including Hilton. (Yield data and photograph courtesy of Dr. Perry Crandall.)

Figure 4:
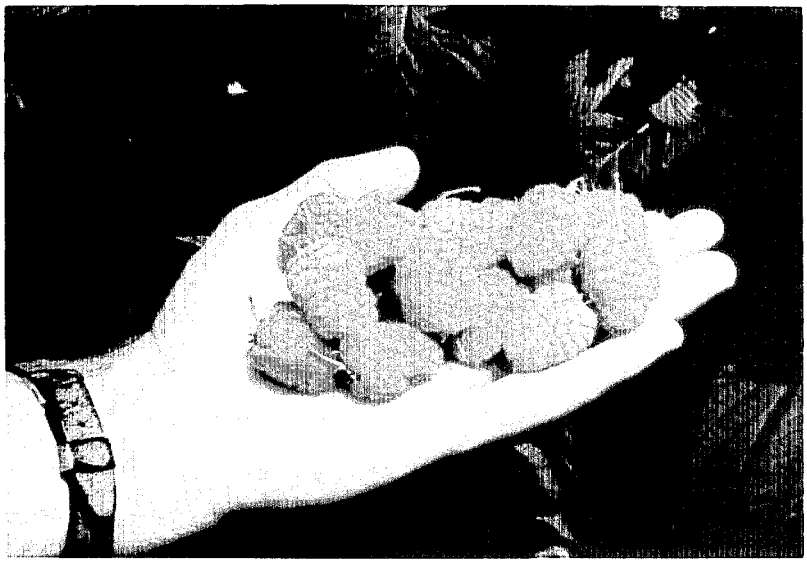

FIG. 4—Fruit of N.Y. 883. Note bright red color, long conic shape, somewhat irregular druplet size, and large fruit size. These fruit are 2.5-3.0 cm. long.

Figure 5:
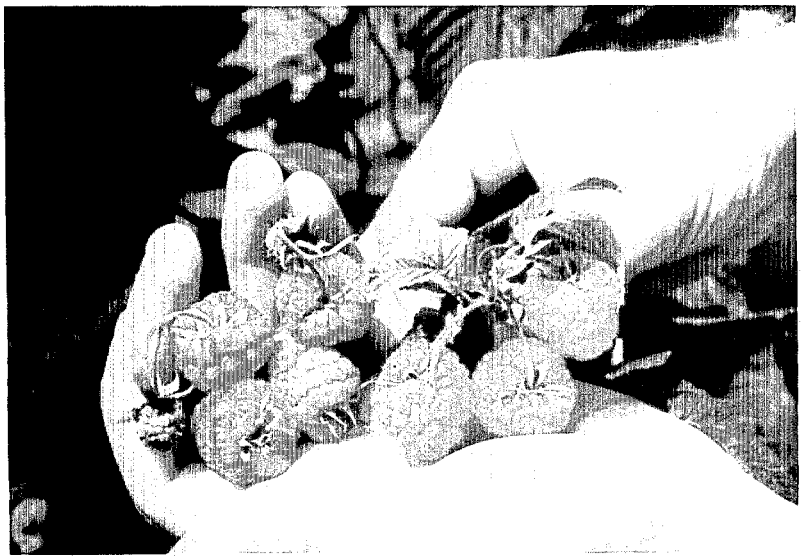

FIG. 5—Receptacle end of N.Y. 883 fruit. Note that, unlike Hilton, fruit are pinched together at the receptacle end, surrounding and firmly clasping the torus and most of the sepals. Relatively firm, large clasping, and pendant fruit along with a long pedicel make it practical for the entire N.Y. 883 fruit to be picked, including torus and pedicel. This can result in minimal fruit damage during harvest and solid berries, well suited for shipping and handling.

MERITS

N.Y. 883 is exceptional relative to its fruit size, its yield potential, and the visibility of its fruit. 'Hilton' is the only variety of red raspberry currently grown on a commercial scale in the United States with comparable fruit size. N.Y. 883 has fruit which is better exposed, firmer, more brightly colored, and has a more desirable fresh fruit flavor than 'Hilton'.

Yield trials conducted by Dr. Perry Crandall at Vancouver, Wash., confirmed that fruit of N.Y. 883 were much larger than the other principal varieties and selections. The same yield trail indicated that N.Y. 883 has exceptional yield potential, and that under certain conditions N.Y. 883 will dramatically outyield other principal varieties and selections, including 'Hilton'.

We claim:

1. The new and distinct variety of red raspberry herein described and illustrated and identified by the characters enumerated above.

* * * * *

UNITED STATES PATENT AND TRADEMARK OFFICE

CERTIFICATE OF CORRECTION

PATENT NO. : Plant Patent No. 5,404

DATED : February 12, 1985

INVENTOR(S) : SANFORD ET AL.

It is certified that error appears in the above-identified patent and that said Letters Patent is hereby corrected as shown below:

Page 1, column 1, line 43, "4-16" should be --4-6--;

Page 2, column 3, line 1, after "large" please insert a comma --,--.

Signed and Sealed this

*Sixteenth* Day of *July 1985*

[SEAL]

*Attest:*

DONALD J. QUIGG

*Attesting Officer* *Acting Commissioner of Patents and Trademarks*